US00RE35176E

United States Patent [19]

Powell

[11] E Patent Number: Re. 35,176

[45] Reissued Date of Patent: Mar. 12, 1996

[54] SELF-VENTING BALLOON DILATATION CATHETER AND METHOD

[75] Inventor: Philip E. Powell, Palo Alto, Calif.

[73] Assignee: Advanced Cardiovascular Systems, Inc., Santa Clara, Calif.

[21] Appl. No.: 827,541

[22] Filed: Jan. 20, 1992

Related U.S. Patent Documents

Reissue of:

[64] Patent No.: 4,638,805
Issued: Jan. 27, 1987
Appl. No.: 760,637
Filed: Jul. 30, 1985

U.S. Applications:

[63] Continuation of Ser. No. 303,384, Jan. 27, 1989, abandoned.

[51] Int. Cl.[6] ..... A61M 29/00

[52] U.S. Cl. ..... 604/96; 606/194

[58] Field of Search ..... 604/96–103, 166, 604/167, 53, 280, 126, 45; 606/191, 194, 195

[56] References Cited

U.S. PATENT DOCUMENTS

| | | | |
|---|---|---|---|
| 3,467,101 | 9/1969 | Fogerty et al. | 128/348.1 |
| 3,794,036 | 2/1974 | Carroll | 128/207.15 |
| 4,160,448 | 7/1979 | Jackson | 128/673 |
| 4,323,071 | 4/1982 | Simpson et al. | 604/96 |
| 4,573,470 | 3/1986 | Samson et al. | 128/657 X |
| 4,582,181 | 4/1986 | Samson | 604/95 |
| 4,597,755 | 7/1986 | Samson et al. | 604/96 |

*Primary Examiner*—Stephen C. Pellegrino
*Assistant Examiner*—William W. Lewis
*Attorney, Agent, or Firm*—Crosby, Heafey, Roach & May

[57] ABSTRACT

Self-venting balloon dilatation catheter having a flexible tubular member with first and second lumens extending therethrough. An inflatable balloon is carried by the distal extremity of the tubular member in such a manner so that the first lumen extends through the balloon and is out of communication with the interior of the balloon and the second lumen is in communication with the interior of the balloon. A venting device is disposed between the balloon and the tubular member for venting air from the interior of the balloon but inhibiting the escape of liquid from the balloon.

24 Claims, 1 Drawing Sheet

SELF-VENTING BALLOON DILATATION CATHETER AND METHOD

Matter enclosed in heavy brackets [ ] appears in the original patent but forms no part of this reissue specification; matter printed in italics indicates the additions made by reissue.

*This is a continuation of the application Ser. No. 07/303, 384 which was filed on Jan. 27, 1989, now abandoned.*

This invention relates to balloon dilatation catheters and more particularly to such catheters having a self-venting balloon and a method for making the same.

In utilizing balloon dilatation catheters, it is necessary that the balloon be filled with a liquid. In the filling of the balloon, it is desirable that the air which is within the balloon be expelled from the balloon but the air is compressible. In the past this has been accomplished by successively aspirating the balloon with fluid. The air is withdrawn during the repeated evacuation. This has a disadvantage in that it can be difficult to ensure complete removal of all the air. Alternatively, the air removal is accomplished by providing a separate tube which may be removable which extends from the proximal extremity of the catheter into the balloon so that during the time that the liquid is being introduced into the balloon, the air in the balloon can be expelled through the separate tube. The use of such a separate tube has a disadvantage, particularly when it is desired to provide a dilatation catheter which has a very low profile in that it makes it more difficult to reduce the profile of the dilatation catheter. There is therefore a need for a new and improved balloon dilatation catheter which overcomes these limitations.

In general it is an object of the present invention to provide a balloon dilatation catheter which is self-venting.

Another object of the invention is to provide a dilatation catheter of the above character in which the air is vented through the distal extremity of the catheter.

Another object of the invention is to provide a balloon dilatation catheter of the above character in which the air in the balloon is vented while the leakage of any liquid from the balloon is inhibited.

Another object of the invention is to provide a balloon dilatation catheter of the above character which ensures complete removal of the air without aspiration.

Another object of the invention is to provide a method for constructing the catheter of the present invention.

Additional objects and features of the invention will appear from the following description in which the preferred embodiment is set forth in detail in conjunction with the accompanying drawing.

In general, the self-venting balloon dilatation catheter of the present invention is comprised of a flexible tubular member having first and second lumens extending therethrough. An inflatable balloon is carried by the distal extremity of the tubular member in such a manner so that the first lumen extends through the balloon and is out of communication with the interior of the balloon and the second lumen is in communication with the interior of the balloon. A vent system is disposed between the balloon and the tubular member for venting air from the interior of the balloon but inhibiting the escape of liquid from the balloon.

Figure 1:
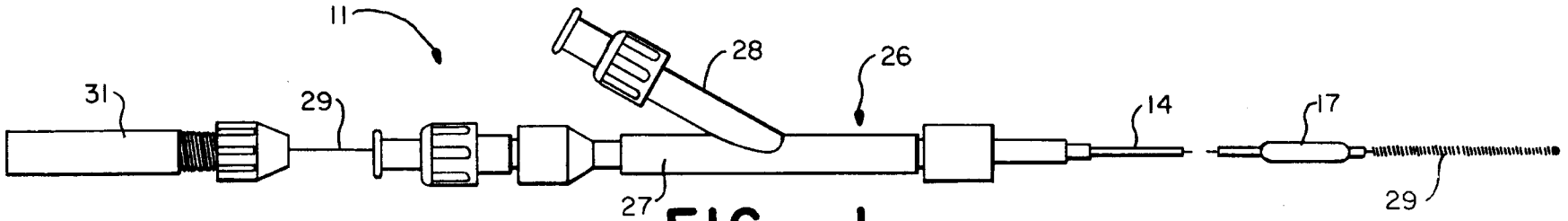
FIG. 1 is a side elevational view of a balloon dilatation catheter incorporating the present invention.
Figure 2:
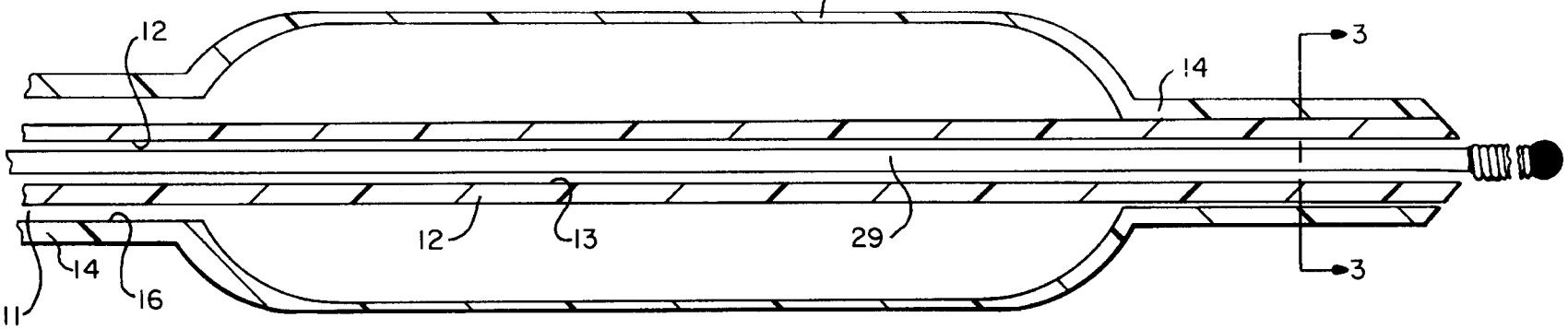
FIG. 2 is a cross sectional view of the distal extremity of the balloon dilatation catheter shown in FIG. 1.
Figure 3:
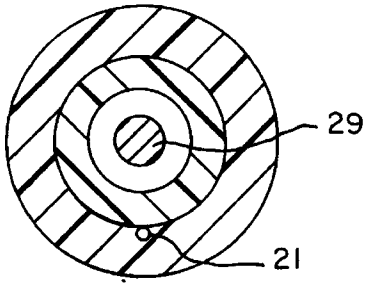
FIG. 3 is a cross sectional view taken along the line 3—3 of FIG. 2.

More in particular as shown in FIGS. 1–3 of the drawing, the balloon dilatation catheter 10 incorporated the present invention is comprised of a tubular member 11 which consists of a first tubular element 12 which has a lumen 13 extending therethrough. It also consists of a second tubular element 14 which is coaxially disposed on the first tubular element 12 and provides in conjunction with the first tubular element an annular lumen which extends longitudinally of the first and second tubular elements 12 and 14. An expandable balloon 17 is carried by the second tubular element 14 of the member 11 near the distal portion thereof and has its interior in communication with the lumen 16. The balloon 17 extends concentrically about the first tubular element 12. Although the balloon 17 can be formed as a separate element which has its extremities bonded to the second tubular element 14, it is preferably formed integral with the second tubular element as shown. The tubular elements 12 and 14 are formed of a suitable flexible thermo-plastic material such as a polyolefin or polyvinychloride.

The distal extremities of the first and second tubular elements 12 and 14 are bonded together in a suitable manner so as to form a liquid-tight seal between the same. Typically this can be accomplished by applying heat to the distal extremity of the second tubular element with a mandrel disposed in the distal extremity of the first tubular element and applying heat to shrink the distal extremity of the second tubular element onto the first tubular element to form such a seal.

Figure 4:
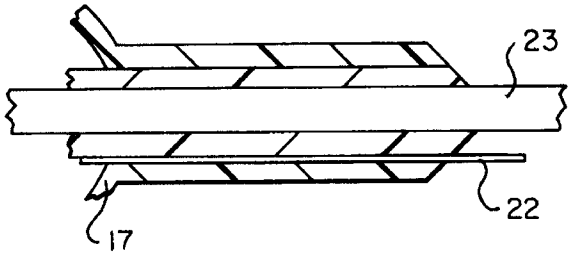
FIG. 4 is a cross sectional view showing the method which is utilized in manufacturing the balloon dilatation catheter shown in FIGS. 1–3.

Means is provided in the distal extremity of the first and second tubular elements for venting air from the balloon 17 while inhibiting the escape of liquid from the balloon 17 and consists of a very small passage 21 which is disposed between the distal extremities of the first and second tubular elements 12 and 14 and which extends from the interior of the balloon 17 to ambient at the distal extremity of the catheter 11. The flow passage 21 can be formed in any suitable manner. One method found to be particularly efficacious is as follows in conjunction with FIG. 4. A piece 22 of suitable wire such as tungsten is used because of its good tensile strength. The wire 22 should have a diameter which is less than 0.001 inches as, for example, 0.0005 inches. It is coated with silicone. After the wire 22 has been coated with silicone, it is inserted by a tweezes between the distal extremities of the first and second tubular elements 12 and 14 prior to the time that the second tubular element 14 is heat shrunk onto the first tubular element as hereinbefore described. As soon as the tungsten wire 22 has been inserted into the distal extremities of the first and second tubular elements 12 and 14 so that it extends into the balloon 17 and out the distal extremities as shown in FIG. 4, a mandrel 23 is inserted into the lumen 13. Heat is then applied to the distal extremity of the second tubular element 14 to cause it to form a shrink fit between it and the distal extremity of the first tubular element 12 and at the same time to shrink down around the wire 22. After the distal extremity of the catheter has been cooled, the mandrel 23 can be removed and the wire 22 can be pulled out with tweezers leaving the cylindrical flow passage 21 hereinbefore described.

It should be appreciated that if desired, more than one hole or passage 21 can be provided to make the balloon venting procedure more rapid. It also should be appreciated that other means can be provided in the distal extremity of the catheter in place of the passage 21 for making the balloon 17 self-venting. For example, braided fibers can be utilized in the distal extremity of the catheter in the same manner as the tungsten wire 22 has been utilized. In such a case, the fibers can be left in place so that the air can flow between interstices of the braided fibers. Alternatively, hollow fiber or fibers can be incorporated into the distal extremity of the catheter. Alternatively, hydrophobic filter material can be incorporated between the distal extremities of the first and second tubular elements 12 and 14. This filter material is capable of passing air but inhibits the passage of liquid from the balloon 17.

The remainder of the balloon dilatation catheter shown in FIG. 1 is substantially conventional. A side arm adapter 26 is provided which has a main or central arm 27 and a side arm 28. A guide wire 29 extends through the main or central arm 27 and extends through the lumen 13 of the first tubular element 12 and has a distal extremity extending beyond the distal extremity of the dilatation catheter 11. A torquer 31 is secured to the proximal extremity of the guide wire 29 and is utilized for extending and retracting the guide wire and also for rotating the guide wire.

Use of the self-venting balloon dilatation catheter may now be briefly described as follows. The balloon 17 is first inflated outside of the human body by introducing a radiographic contrast liquid through the side arm 28 so that it passes through the annular lumen 16 between the first and second tubular elements 12 and 14 and passes into the balloon 17. The air which is in the balloon is pushed forwardly in the balloon and under the pressure of the radiographic contrast liquid is forced to pass out through the small passage 21 provided between the distal extremities of the first and second tubular elements 12 and 14. By utilizing a passage 21 having a diameter of 0.0005 inches, it has been found that a two millimeter diameter balloon having a length of approximately 25 millimeters can be completely rid of air in less than approximately 40 seconds. The size of the passage 21 is such that it inhibits the escape of the radiographic contrast liquid so that very little, if any, of the liquid can escape, even though pressure up to 200 psi for the radiographic contrast liquid is attained within the balloon 17. As soon as the balloon 17 has been inflated with the radiographic contrast liquid and the air has been expelled therefrom through the passage 21, the liquid can be withdrawn to deflate the balloon 17. The balloon dilatation catheter is now ready to be inserted into the human body. After the balloon 17 has been positioned in the stenosis in the arterial vessel in the human body, the balloon can be again inflated by reintroducing radiographic contrast liquid through the side arm 28 through the lumen 16 and into the balloon 17. Since all of the air has previously been expelled from the balloon 17, the balloon can be readily inflated within the stenosis to its full diameter at the desired pressure as, for example, in excess of 100 psi without danger of any significant amount of radiopaque contrast liquid passing through the passage 21. After the opening in the stenosis has been enlarged, the balloon can be deflated and the dilatation catheter can be removed.

It is apparent from the foregoing that there has been provided a balloon dilatation catheter which is self-venting and in which the balloon can be inflated to the desired pressure without danger of any significant amount of radiopaque contrast liquid passing through the venting orifice provided in the distal extremity of the balloon dilatation catheter. The venting orifice formed in the distal extremity of the balloon dilatation catheter is formed in such a manner sot that it can be readily incorporated into the manufacturing process for making the balloon dilatation catheters.

What is claimed is:

1. In a self-venting balloon dilatation catheter, a flexible tubular member having first and second lumens extending therethrough, an inflatable balloon carried by the distal extremity of the tubular member in such a manner so that the first lumen extends through the balloon and is out of communication with [that] *the* the interior of the balloon and the second lumen is in communication with the [distal extremity] interior of the balloon and [means disposed between the balloon and tubular member] *a passageway having a transverse cross-sectional dimension less than about 0.001 inch extending from the interior of the balloon to ambient* for venting air from the interior of the balloon but inhibiting the escape of liquid from the balloon.

2. A dilatation catheter as in claim 1 wherein said means is disposed between the balloon and a tubular member for venting air comprised of a flow passage having a diameter of less than approximately 0.001 inch.

3. A dilatation catheter as in claim 2 wherein said means is disposed between the balloon and the tubular member includes hydrophobic material.

4. A dilatation catheter as in claim 1 wherein said tubular member is comprised of a first tubular element having the first lumen extending therethrough, a second tubular element coaxially disposed over said first tubular element and forming the second lumen extending between the first and second tubular members and wherein the expandable balloon is carried by the second tubular element and has its interior in communication with the second lumen between the first and second tubular elements.

5. In a self-venting balloon dilatation catheter, a first tubular element having a lumen extending therethrough, a second tubular element coaxially disposed over said first tubular element and forming a lumen extending between the first and second tubular members, an expandable balloon carried by the second tubular element and having its interior in communication with the lumen between the first and second tubular elements and means disposed between the distal extremities of the first and second tubular elements for venting air from the interior of the balloon but inhibiting escape of a liquid from the balloon.

6. A dilatation catheter as in claim 5 wherein said means disposed between the distal extremities of the first and second tubular elements for venting air comprises a flow passage having a diameter less than approximately 0.001 inches.

7. A dilatation catheter as in claim 6 wherein said means disposed between the distal extremities of the first and second tubular elements includes hydrophobic material.

8. A balloon dilatation catheter as in claim 5 wherein said means disposed between the distal extremities of the first and second tubular elements for venting air includes members disposed between the first and second tubular elements permitting the escape of air from the interior of the balloon but inhibiting the escape of liquids from the balloon.

9. A dilatation catheter as in claim 5 wherein said first and second tubular elements are formed of thermoplastic materials.

10. A dilatation catheter as in claim 9 wherein the distal extremities of the first and second tubular elements are sealed by a heat shrink seal.

*11. A self-venting vascular comprising:*

*a) a flexible tubular member having at least one inner lumen extending therethrough to an interior portion of the catheter with means to receive liquid under pressure;*

*b) a venting means with a flow restrictive passageway having a transverse cross-sectional dimension less than about 0.001 inch extending from the interior portion of*

*the catheter to ambient which allows air but no substantial amount of liquid to pass therethrough while a pressure in excess of 100 psi is maintained in the interior of the catheter.*

*12. The self-venting catheter of claim 11 wherein the flow restrictive passageway of the venting means has circular transverse cross-sectional shape with a diameter of less than about 0.001 inch.*

*13. The self-venting catheter of claim 11 wherein the flow restrictive passageway of the venting means includes braided fibers.*

*14. The self-venting catheter of claim 11 wherein the flow restrictive passageway of the venting means includes hydrophobic filter material.*

*15. The self-venting catheter of claim 11 wherein the flow restrictive passageway of the venting means will allow no substantial amounts of inflating liquid to pass therethrough at pressures in excess of 100 psi.*

*16. In a balloon dilatation catheter comprising an elongated tubular member with an inflatable balloon on the distal portion thereof and with an inner lumen extending therein which is in fluid communication with the interior of the balloon and which directs inflating liquid therein, the improvement comprising an air venting means which includes at least one flow restrictive passageway having a transverse cross-sectional dimension less than about 0.001 inch extending between the balloon interior and ambient which allows air but no substantial amounts of inflating liquid to pass therethrough while a pressure in excess of 100 psi is maintained in the balloon interior.*

*17. The balloon dilatation catheter of claim 16 wherein the flow restrictive passageway has a circular transverse shape with a diameter less than about 0.001 inch.*

*18. The balloon dilatation catheter of claim 16 wherein the flow restrictive passageway contains braided fibers.*

*19. The balloon dilatation catheter of claim 16 wherein the flow restrictive passageway contains hydrophobic filter material.*

*20. The balloon dilatation catheter of claim 16 wherein a plurality of flow restrictive passageways are provided.*

*21. The balloon dilatation catheter of claim 16 wherein the flow restrictive passageway will allow no substantial amounts of inflating liquid to pass therethrough at liquid pressures in excess of 100 psi.*

*22. The balloon dilatation catheter of claim 16 wherein the flow restrictive passageway extends in a distal direction from the interior of the balloon.*

*23. The balloon dilatation catheter of claim 16 wherein the balloon has a distal end which is sealingly bonded to an inner member.*

*24. The balloon dilatation catheter of claim 23 wherein the flow restrictive passageway of the venting means extends from the interior of the balloon to ambient in a distal direction between the distal end of the balloon and the inner member.*

* * * * *

UNITED STATES PATENT AND TRADEMARK OFFICE

CERTIFICATE OF CORRECTION

PATENT NO. : Re. 35,176
DATED : March 12, 1996
INVENTOR(S) : Philip E. Powell

It is certified that error appears in the above-indentified patent and that said Letters Patent is hereby corrected as shown below:

On the title page, item "[22] Filed: Jan. 20, 1992" should be --Jan. 29, 1992--; and Column 4, line 60, after "vascular" insert --catheter--.

Signed and Sealed this

Sixteenth Day of September, 1997

*Attest:*

Bruce Lehman

BRUCE LEHMAN

*Attesting Officer*

*Commissioner of Patents and Trademarks*